(12) United States Patent
Majeed et al.

(10) Patent No.: US 8,933,121 B2
(45) Date of Patent: Jan. 13, 2015

(54) ANTI-OBESITY POTENTIAL OF CALEBIN A

(75) Inventors: Muhammed Majeed, Edison, NJ (US); Anjali Pandey, Bangalore (IN)

(73) Assignee: Sami Labs Limited, Karnataka (IN)

(*) Notice: Subject to any disclaimer, the term of this patent is extended or adjusted under 35 U.S.C. 154(b) by 0 days.

(21) Appl. No.: 13/347,071

(22) Filed: Jan. 10, 2012

(65) Prior Publication Data

US 2013/0012579 A1     Jan. 10, 2013

Related U.S. Application Data

(60) Provisional application No. 61/431,157, filed on Jan. 10, 2011.

(51) Int. Cl.
    *A61K 31/235*     (2006.01)
    *A61K 31/215*     (2006.01)
    *C12N 5/077*     (2010.01)

(52) U.S. Cl.
    CPC ............ *A61K 31/235* (2013.01); *C12N 5/0653* (2013.01); *C12N 2500/76* (2013.01)
    USPC ............ 514/543; 514/506; 514/529; 514/532

(58) Field of Classification Search
    USPC .................................. 514/506, 529, 532, 543
    See application file for complete search history.

(56) References Cited

U.S. PATENT DOCUMENTS

| | | | |
|---|---|---|---|
| 6,887,898 B1 * | 5/2005 | Kim | 514/545 |
| 7,572,829 B2 * | 8/2009 | Kim | 514/532 |
| 7,728,043 B2 * | 6/2010 | Kim | 514/678 |
| 8,206,753 B2 * | 6/2012 | Tripp et al. | 424/725 |
| 2005/0238654 A1 * | 10/2005 | Takeda | 424/195.15 |
| 2009/0028896 A1 * | 1/2009 | Takeda | 424/195.15 |
| 2012/0035274 A1 * | 2/2012 | Park | 514/766 |

OTHER PUBLICATIONS

Yuliana et al., Screening of selected Asian spices for anti obesity-related bioactivities, Jun. 15, 2011, Food Chemistry, vol. 126, Issue 4, pp. 1724-1729.*

* cited by examiner

*Primary Examiner* — My-Chau T Tran

(57) ABSTRACT

The present invention discloses the potential of Calebin A in inhibiting adipogenesis and applications thereof in obesity management. The present invention elucidates the potential of Calebin A to favorably modulate biochemical markers associated with obesity. Notable biomodulatory properties of Calebin A include inhibiting leptin production, increasing adiponectin expression and inhibiting local (adipocyte) and systemic inflammation caused by pro-inflammatory cytokines Tumor Necrosis Factor (TNF-$\alpha$), Interleukin-6 (IL-6) and Interleukin-1 (IL-1$\beta$).

12 Claims, 7 Drawing Sheets

ANTI-OBESITY POTENTIAL OF CALEBIN A

This application is a non-provisional filing of provisional application 61/431,157 filed on Jan. 10, 2011.

FIELD OF INVENTION

The invention in general relates to medicaments for obesity management. More specifically, it relates to anti-obesity potential of Calebin A.

DESCRIPTION OF PRIOR ART

Obesity is the most prevalent nutritional disorder in industrialized countries and is a growing problem in developing countries. It is described as a global epidemic and overweight and obese individuals (BMI of 25 and above) are at increased risk for various chronic physical ailments and psychological problems such as depression, eating disorders and low self esteem. It is associated with various diseases like cardiovascular diseases, diabetes mellitus, osteoarthritis, obstructive sleep apnea and cancer. WHO considers obesity to be one of the top 10 causes of preventable death worldwide.

In obesity, there is an increase in the adipose tissue mass due to the production of new fat cells (adipocytes) through the process of adipogenesis and/or the deposition of increased amounts of cytoplasmic triglyceride per cell. A fat cell develops as internally produced lipid droplets coalesce into a single large mass. Eventually, cellulite results due to enhanced adipogenesis and accumulation of chunks of adipocytes under the skin dermis.

Studies of adipogenesis have proceeded with the hope that manipulation of this process in humans might lead to a reduction in the burden of obesity and diabetes. At molecular level, several markers have been targeted in treating obesity such as leptin, adiponectin, TNF-$\alpha$ etc Though drugs are available for treating the disorder, there is a constant need and search for safe natural approach to help manage obesity and its related socio-economic consequences.

Calebin A is known to protect neuronal cells from $\beta$-amyloid insult (Park S Y et al, J Nat Prod. 2002 September; 65(9):1227-31), induce apoptosis and modulate MAPK family activity in drug resistant human gastric cancer cells (Li Y et al, *Eur J. Pharmacol.* 2008 Sep. 4; 591(1-3):252-8). Zeng Y et al. (Chem Pharm Bull (Tokyo) 2007 June; 55(6):940-3) discusses two new calebin derivatives, 4"-(4'"-hydroxyphenyl-3'"-methoxy)-2"-oxo-3"-butenyl-3-(4'-hydroxyphenyl)-propenoate and 4"-(4'"-hydroxyphenyl)-2"-oxo-3"-butenyl-3-(4'-hydroxyphenyl-3'-methoxy)-propenoate.

The present invention discloses the potential of Calebin A to prevent fat accumulation during the terminal differentiation of adipocytes (fat cells) and applications thereof in obesity management. The present invention elucidates the potential of Calebin A to favorably modulate biochemical markers associated with obesity. Notable biomodulatory properties of Calebin A include inhibiting leptin production, increasing adiponectin expression and inhibiting local (adipocyte) and systemic inflammation caused by pro-inflammatory cytokines Tumor Necrosis Factor (TNF-$\alpha$), Interleukin-6 (IL-6) and Interleukin-1 (IL-1$\beta$).

Accordingly, it is the principle objective of the present invention to disclose anti-obesity potential of Calebin A.

The invention fulfills the aforesaid principle objective and provides further related advantages.

SUMMARY OF THE INVENTION

The present invention discloses the potential of Calebin A in inhibiting adipogenesis and applications thereof in obesity management. The present invention elucidates the potential of Calebin A to favorably modulate biochemical markers associated with obesity in mammals. Notable biomodulatory properties of Calebin A include inhibiting leptin production, increasing adiponectin expression and inhibiting local (adipocyte) and systemic inflammation caused by pro-inflammatory cytokines Tumor Necrosis Factor (TNF-$\alpha$), Interleukin-6 (IL-6) and Interleukin-1 (IL-1$\beta$).

Other features and advantages of the present invention will become apparent from the following more detailed description, taken in conjunction with the accompanying drawings, which illustrate, by way of example, the principle of the invention.

DETAILED DESCRIPTION OF INVENTION

The present invention discloses the potential of Calebin A to prevent fat accumulation during the terminal differentiation of adipocytes (fat cells) and applications thereof in obesity management. The present invention elucidates the potential of Calebin A to favorably modulate biochemical markers associated with obesity. Notable biomodulatory properties of Calebin A include inhibiting leptin production, increasing adiponectin expression and inhibiting local (adipocyte) and systemic inflammation caused by pro-inflammatory cytokines Tumor Necrosis Factor (TNF-$\alpha$), Interleukin-6 (IL-6) and Interleukin-1 (IL-1$\beta$).

Figure 1:
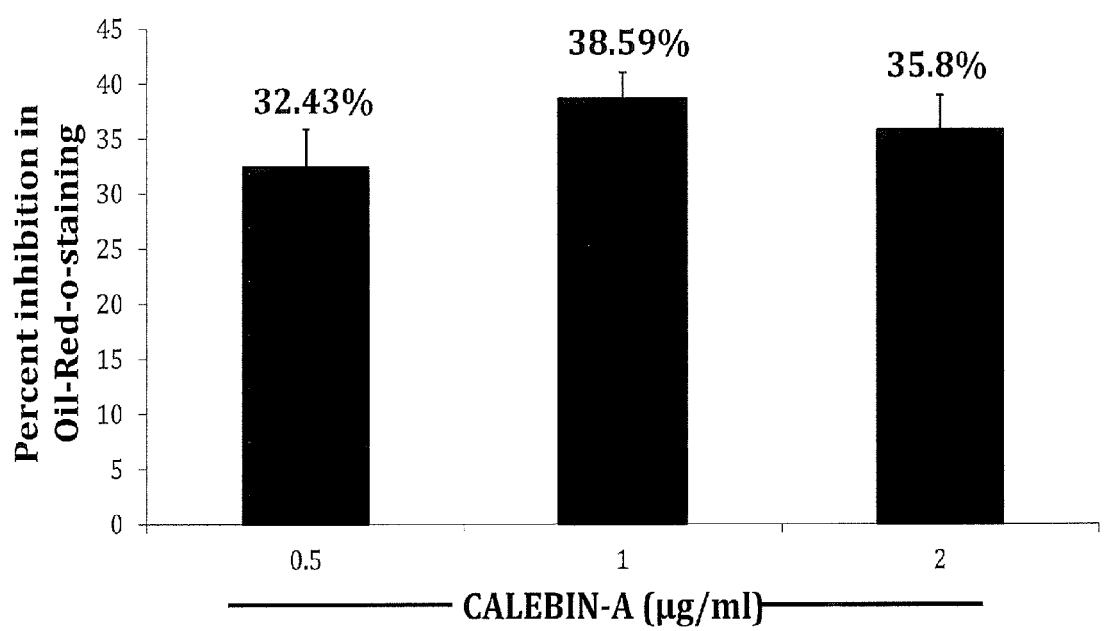
FIG. 1 shows the graphical representation of the percentage adipogenesis inhibition effected by Calebin A at concentrations of 0.5, 1.0 and 2.0 µg/ml as studied by the Oil-Red-O-Staining method.

In the most preferred embodiment, the present invention relates to a method of inhibiting adipogenesis, said method comprising step of bringing into contact the adipocytes with an effective amount of Calebin A. In other words, the present invention relates to a method of preventing accumulation of fat during the terminal differentiation of mammalian adipocytes. (FIG. 1).

Figure 2:
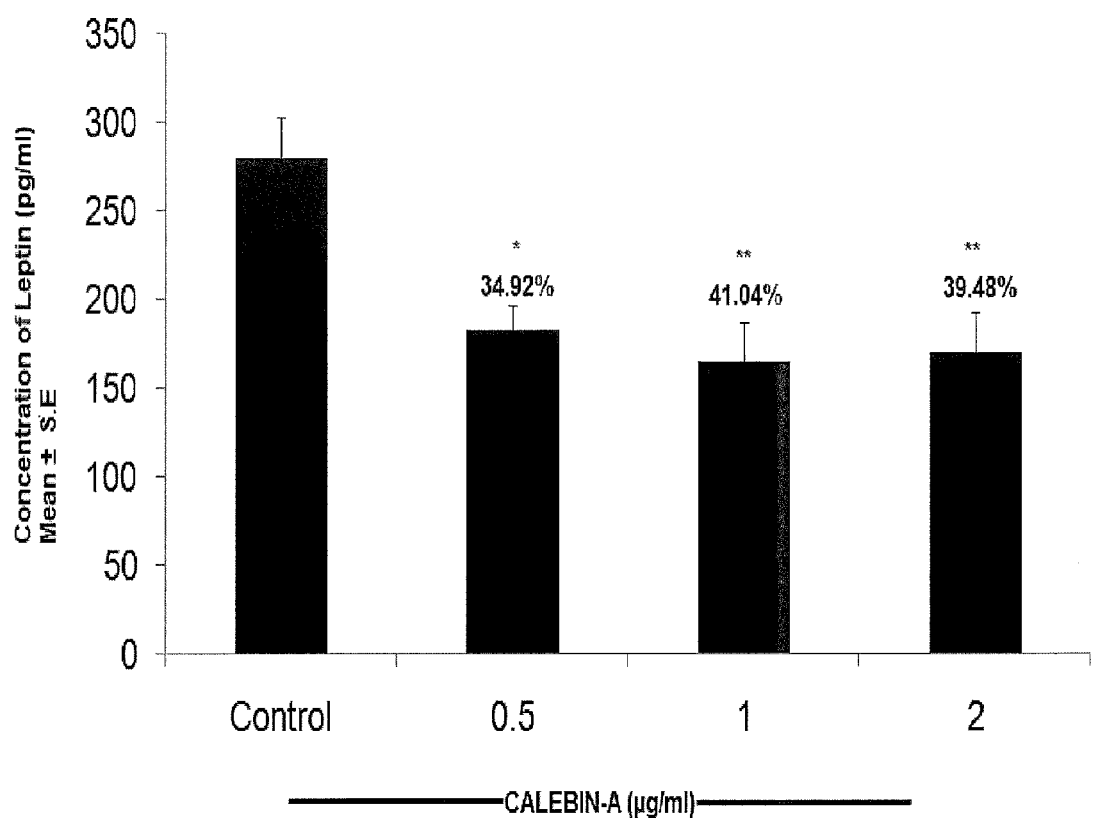
FIG. 2 shows the graphical representation of the percentage inhibition of leptin production in human adipocytes effected by Calebin A at concentrations of 0.5, 1.0 and 2.0 µg/ml. P value *:<0.01; **:<0.001.

In another preferred embodiment, the present invention relates to a method of inhibiting leptin expression in adipocytes, said method comprising step of bringing into contact the adipocytes with an effective amount of Calebin A (FIG. 2).

Figure 3:
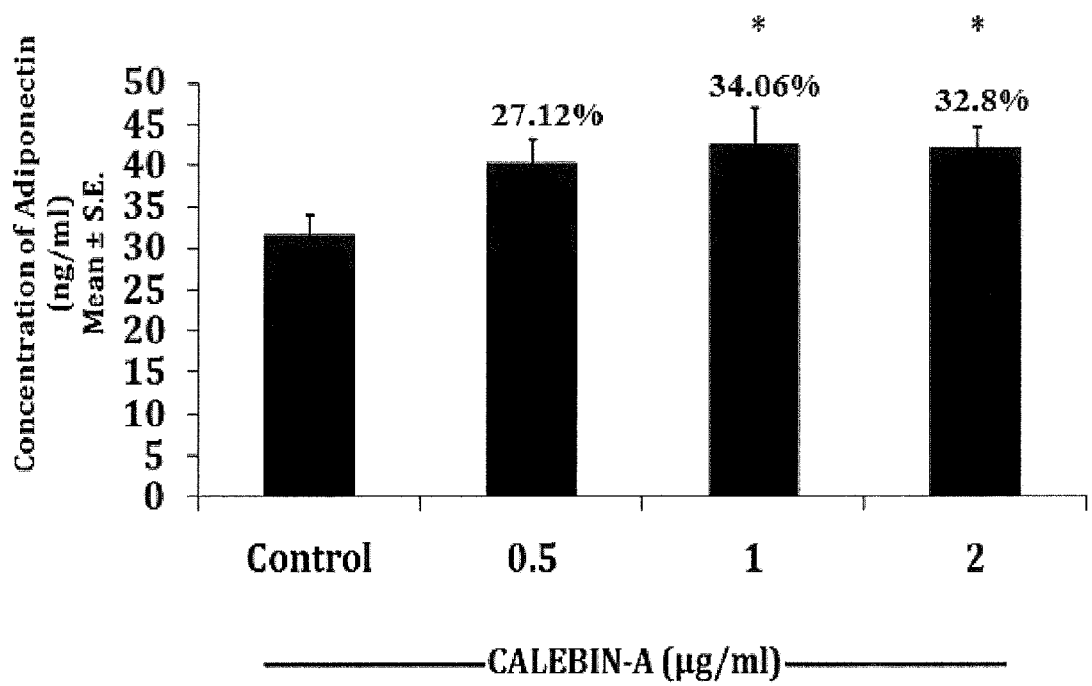
FIG. 3 shows the graphical representation of the percentage increase of adiponectin expression in human adipocytes effected by Calebin A at concentrations of 0.5, 1.0 and 2.0 µg/ml. P value *:<0.01.

In another preferred embodiment, the present invention relates to a method of increasing expression of adiponectin in adipocytes, said method comprising step of bringing into contact the adipocytes with an effective amount of Calebin A (FIG. 3).

Figure 4:
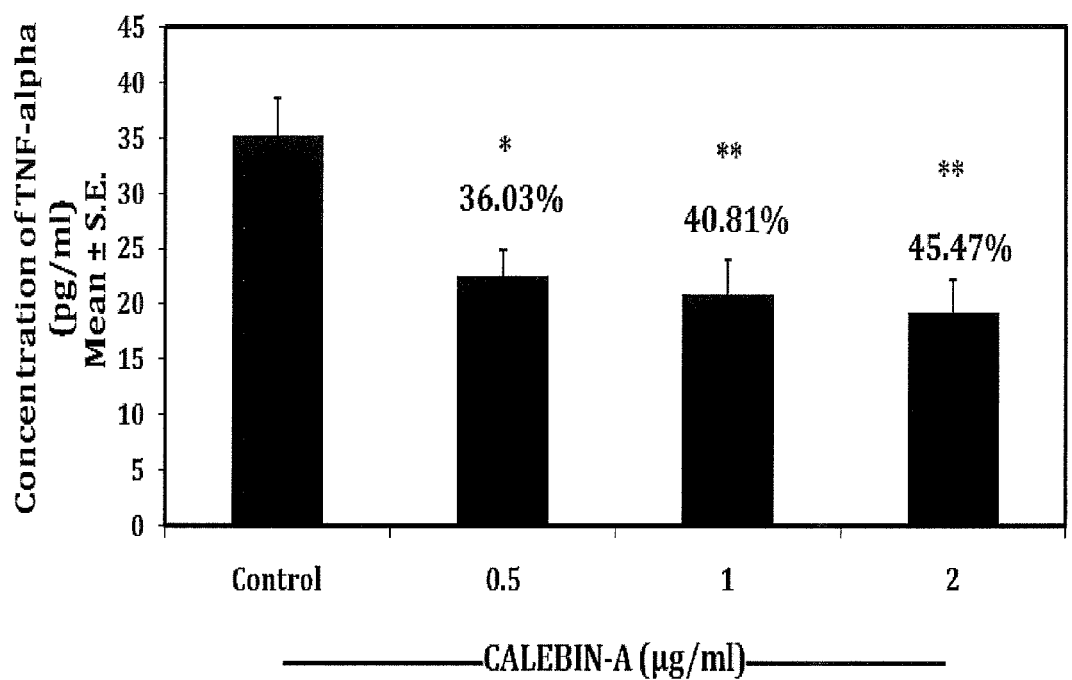
FIGS. 4 and 5 shows the graphical representation of the percentage inhibition of TNF-$\alpha$ expression (P value *:<0.01; **:<0.001) and IL-6 expression (P value *:<0.01) respectively, in human adipocytes effected by Calebin A at concentrations of 0.5, 1.0 and 2.0 µg/ml.

In another preferred embodiment, the present invention relates to a method of inhibiting pro-inflammatory cytokine TNF-α expression in adipocytes, said method comprising step of bringing into contact the adipocytes with an effective amount of Calebin A (FIG. 4).

Figure 5:
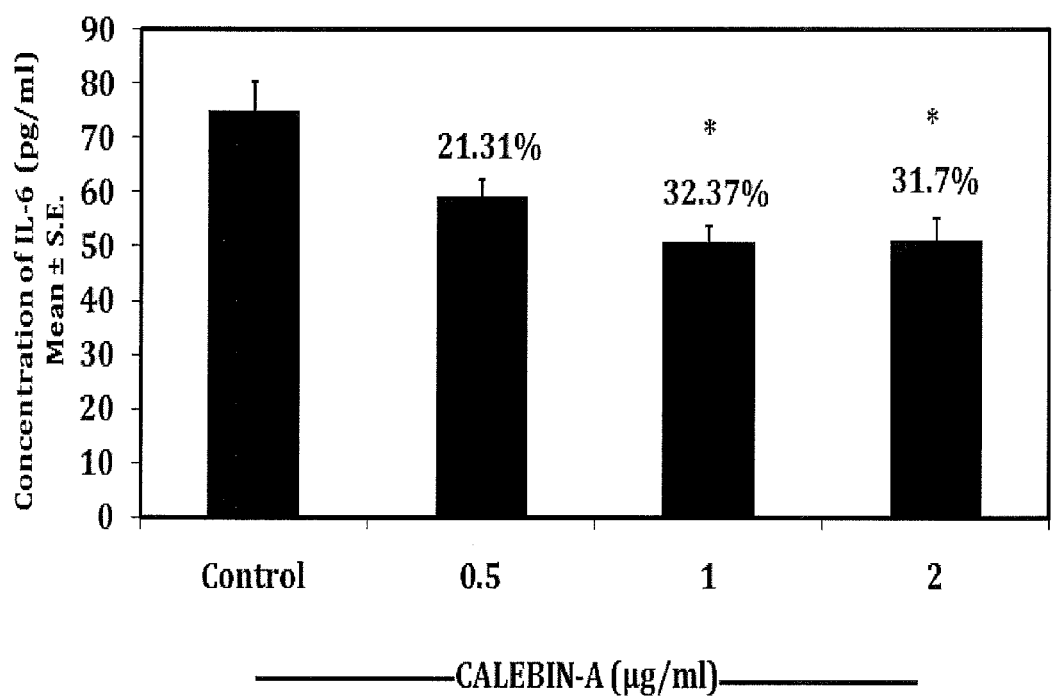

In yet another preferred embodiment, the present invention relates to a method of inhibiting pro-inflammatory cytokine Interleukin-6 expression in adipocytes, said method comprising step of bringing into contact the adipocytes with an effective amount of Calebin A (FIG. 5).

In specific embodiment, the adipocytes referred to herein above are human adipocytes.

In yet another preferred embodiment, the present invention relates to a method of reducing obesity induced systemic expression of pro-inflammatory cytokines in mammals, said method comprising step of administering an effective amount of Calebin A to a subject in need thereof. In specific embodiments, the pro-inflammatory cytokines referred to herein in this paragraph include Tumor Necrosis Factor-α (TNF-α), Interleukin-6 (IL-6) and Interleukin-1β (IL-1β) [FIGS. 6 and 7].

In yet another preferred embodiment, the present invention relates to a method of obesity management, said method comprising step of administration of an effective amount of Calebin-A to a subject in need thereof.

In yet another preferred embodiment, the subject is a mammal.

In yet another preferred embodiment, the subject is a human.

The potential therapeutic value of Calebin A as an anti-obesity molecule may be understood through specific examples elucidated herein below.

EXAMPLE I

Acute Oral Toxicity of Calebin A

Table I lists the parameters studied for Acute Oral Toxicity of Calebin A.
Results:
No mortality was observed up to 2000 mg/kg p.o. in mice up to two weeks of observation.

TABLE I

| parameters studied for Acute Oral Toxicity of Calebin A | |
|---|---|
| General Behavior | Dermal |
| Aggression = Nil | Blanching = Nil |
| Fear = Nil | Hyperaemia = Nil |
| Passive = Nil | Cyanosis = Nil |
| General Movement = Normal | |
| General Locomotor Activity = Normal | |
| Central Nervous System | General Observations |
| Excitation = Nil | Muscular Weakness = Nil |
| Motor Activity = Nil | Salivation = Nil |
| Tremors = Nil | Pilo-erection = Nil |
| Clonic Convulsions = Nil | Diarrhea = Nil |
| Tonic Convulsions = Nil | |

TABLE I-continued

| parameters studied for Acute Oral Toxicity of Calebin A | |
|---|---|
| Respiratory System | Reflexes |
| Respiration Rate = Normal | Corneal = No effect |
| Respiration Depth = Normal | Pinnal = No effect |
| Autonomic Nervous System | Food and Water (Intake and Excretion) |
| Motor activity = Normal | Fecal Output = Normal |
| Atexia = Nil | Urine Output = Normal |
| Respiration Rate = Normal | |
| Diarrhea = Nil | |

EXAMPLE II

Oil-Red-O-Staining of Adipogenic Cultures and Estimation of Leptin, Adiponectin, TNF-α and IL-6 by ELISA Terminal differentiation of adipocytes is accompanied by the accumulation of great amounts of lipids in large cytoplasmic vesicles. A common assay to measure adipocyte differentiation in cell culture is with the dye Oil Red-O (ORO). ORO is a lipid-soluble bright red dye which is a reliable indicator of adipocyte differentiation (adipogenesis).
Principle:

Oil Red O (Solvent Red 27, Sudan Red 5B, C.I. 26125, and C26H24N4O) is a lysochrome (fat-soluble dye) diazo dye used for staining of neutral triglycerides and lipids on frozen sections and some lipoproteins on paraffin sections. It has the appearance of a red powder with maximum absorption at 518(359) nm. Oil Red O is one of the dyes used for Sudan staining. Similar dyes include Sudan III, Sudan IV, and Sudan Black B. The staining has to be performed on fresh samples, as alcohol fixation removes the lipids. Oil Red O largely replaced Sudan III and Sudan IV, as it provides much deeper red color and the stains are therefore much easier to see.

Oil red O is an oil soluble dye. Oil soluble dyes exhibit greater solubility of the dye in lipid substances in the tissues/cells, than in the usual hydro alcoholic dye solvents. Hence, it will deeply stain the cells.
Methodology:

3T3-L1 cells approximately 60×104 cells are seeded for 48-72 hrs to get 70-80% confluence. After 48 hrs 200 µl of AIM (Adipogenesis induction medium) freshly prepared is added. 72 hrs later 200 µl APM (Adipogenesis progression medium) with the test compounds in different concentrations is added to the wells. The cells are incubated for 48 hrs in a humidified atmosphere (370 C) of 5% CO2 and 95% air. The supernatant is collected and stored for the estimation of leptin, adiponectin, IL-6 and TNF-α by ELISA. Cells are fixed by adding 100 µl of 10% formalin and ORO staining is done. OD is read at 492 nm in microplate reader. The results are expressed as $IC_{50}$ values using Graphpad prism software.

The percentage of inhibition of adipogenesis is calculated as follows, $$\% \text{ Inhibition} = C\text{-}T \times 100 \; T$$

Where C-absorbance of Oil red O in differentiating/undifferentiated cells

T-absorbance of Oil red O in sample treated differentiating/undifferentiated cells. The estimation of leptin, adiponectin, IL-6 and TNF-α is done according to user's manual from R&D Systems.

References:
1. Wu Z, Xie Y, Morrison R F, Bucher NLR, Farmer SR 1998. PPAR γ induces the Insulin-dependent Glucose Transporter GLUT4 in the absence of C/EBP☐ during the conversion of 3T3 fibroblasts into adipocytes. J Clin Invest. 101:22-32.
2. A pre-adipose 3T3 cell variant highly sensitive to adipogenic factors & to human growth hormone. L A Salazar-Olivo, F Castro-Munozledo & W Kuri-Harcuch. Department of Cell Biology, Centro de Investigation y de Estudios Avanzados del I.P.N., Mexico D.F., Mexico. Journal of Cell Science, Vol 108, Issue 5 2101-2107.
3. A Nuclear Receptor Atlas: 3T3-L1 Adipogenesis. Mingui Fu, Tingwan Sun, Angie L. Bookout, Micheal Downes, Ruth T. Yu, Ronald M. Evans and David J. Mangelsdorf. Molecular Endocrinology 19 (10): 2437-2450.
4. Aimee D, Kohn et al, JBC, Vol 271, No. 49, pp-31372-31378.

Result:
FIG. 1 shows percentage adipogenesis inhibition of 32.43%, 38.59% and 35.8% respectively effected by Calebin A at concentrations of 0.5, 1.0 and 2.0 µg/ml studied by the Oil-Red-O-Staining method.

FIG. 2 shows percentage inhibition of leptin production (34.92%, 41.04% and 39.48% respectively) in human adipocytes by Calebin A at concentrations of 0.5, 1.0 and 2.0 µg/ml. The importance of the effects of Calebin A in inhibiting leptin production in human adipocytes and correlation thereof to obesity management stems from the following facts (Notes on Pathophysiology of the Endocrine System, Colorado State University).

Leptin is a protein hormone expressed predominantly in adipocytes. It has important effects in regulating body weight, metabolism and reproductive function. Encoded by the obese (ob) gene, the protein is approximately ~16 kDa in mass. At normal concentrations, Leptin's biological function is predominantly vested in its effects on hypothalamic centers of the brain that control hunger, appetite, regulation of body temperature and energy metabolism. Thus leptin, in a non-obese individual could result in weight loss by two important mechanisms. (i) Decrease in hunger and food consumption most probably through the inhibition of neuropeptide Y that controls feeding behavior and (ii) increase in energy expenditure through increased body temperature, oxygen consumption and loss of adipose tissue mass. However, excessive secretion of leptin as in case of obesity or experimental models of induced obesity leads to disrupted functions of hypothalamic centers that an obese subject fails to attain satiations and tends to go on a over feeding mode. Hence it becomes imperative to bring about effective reduction of the over excessive levels of leptin in obesity and Calebin A shows promise in this area as indicated in FIG. 2.

FIG. 3 shows percentage enhancement of adiponectin expression (27.12%, 34.06% and 32.8% respectively) in human adipocytes by Calebin A at concentrations of 0.5, 1.0 and 2.0 µg/ml. Adiponectin is a cytokine produced almost exclusively by adipocytes and is expressed in very high levels by lean and healthy individuals. Obese individuals on the other hand express reduced levels of this adipokine and are prone to coronary heart disease (CAD), diabetes mellitus and hypertension.

References:
1. Tamar. R. Aprahamian and Flora Sam, "Adiponectin in Cardiovascular Inflammation and Obesity, Int J. Inflam. 2011; 2011: 376909;
2. Hotta K, Funahashi T, Arita Y, et al. Plasma concentrations of a novel, adipose-specific protein, adiponectin, in type 2 diabetic patients. Arteriosclerosis, Thrombosis and Vascular Biology. 2000; 20(6):1595-1599;
3. Iwashima Y, Katsuya T, Ishikawa K, et al. Hypoadiponectinemia is an independent risk factor for hypertension. Hypertension. 2004; 43(6):1318-1323;
4. Kumada M, Kihara S, Sumitsuji S, et al. Association of hypoadiponectinemia with coronary artery disease in men. Arteriosclerosis, Thrombosis and Vascular Biology. 2003; 23(1):85-89 and
5. Lindsay R S, Funahashi T, Hanson R L, et al. Adiponectin and development of type 2 diabetes in the Pima Indian population. The Lancet. 2002; 360(9326):57-58.

Calebin A is shown (FIG. 3) to effectively increase levels of adiponectin in human adipocytes and thus show promise in the area of obesity management.

FIGS. 4 and 5 show the percentage inhibition of TNF-α (36.03%, 40.81% and 45.47% respectively) and IL-6 (21.31%, 32.37% and 31.7% respectively) by Calebin A at concentrations of 0.5, 1.0 and 2.0 µg/ml. Bastard J P et al, "Recent Advances in the relationship between obesity, inflammation and insulin resistance", Eur Cytokine Netw. 2006 March; 17(1):4-12 cite that obesity is associated with low-grade inflammation of the white adipose tissue (WAT). The authors also remark that in obesity, WAT is characterized by increased expression of pro-inflammatory molecules like TNF-α and IL-6 which not only exert effects on WAT but also on other systemic organs of the body. FIGS. 4 and 5 demonstrate that Calebin A is effective in reducing TNF-α and IL-6 expression in adipocytes and would be a useful agent to modulate effects of local and systemic inflammation in obesity.

EXAMPLE III

Modulation of Systemic Inflammation by Calebin A

The present inventors also adduce extra evidence to support the ability of Calebin A to suppress intracellular TNF and extracellular IL-1β in murine neutrophil systems (Table II, Table III). Neutrophils are isolated by histopaque gradient method tested for their ability to produce in vitro TNF-α following stimulation with Lipopolysaccharide (LPS). The cells were incubated with phycoerythrin (PE)-labeled anti-mouse TNF-α. in the dark, and after being washed with sterile PBS, samples were resuspended in PBS (pH 7.4) and acquired directly on the flow cytometer (BDLSR; Becton Dickinson). A fluorescence trigger was set on the PE (FL1) parameter of the gated neutrophil populations (10,000 events). Rolipram at 100 µg/ml was used as standard inhibitor of TNF-α in this study. Fluorescence compensation, data analysis, and data presentation were performed using Cell Quest Pro software (Becton Dickinson).

REFERENCES

1. Clara, B., R. C. Arancha, G. M. Andre's, P. Atanasio, A. Julia, and O. Alberto. 2003. A new method for detecting TNF-α-secreting cells using direct immunofluorescence surface membrane stainings. J. Immuno. Methods 264:77-87.
2. Khurshid A. Bhat, Bhahwal A. Shah, Kuldeep K. Gupta, Anjali Pandey, Sarang Bani, Subhash C. Taneja. Semisynthetic analogs of pinitol as potential inhibitors of TNF-α cytokine expression in human neutrophils. Bioorganic & Medicinal Chemistry Letters 19 2009, 1939-1943.

TABLE II

| Serial No | Sample | Concentration (µg/ml) | Expression of TNF-α Mean ± S.E | % Activity |
|---|---|---|---|---|
| 1 | LPS Control | — | 2.62 ± 0.01 | — |
| 2 | Calebin A | 0.5 | 1.87 ± 0.04* | 28.62%↓ |
| 3 | Calebin A | 1.0 | 1.70 ± 0.02** | 35.11%↓ |
| 4 | Calebin A | 2.0 | 1.59 ± 0.05** | 39.31%↓ |
| 5 | Rolipram | 100 | 0.73 ± 0.09** | 72.13%↓ |

%↓: indicates suppression of TNF-α expression
No. of observations = 3
P-value: *<0.01; **<0.001 students 't' test

TABLE III

| Samples Treatment | Concentration (pg/ml) | % Activity |
|---|---|---|
| LPS Control | 51.80 ± 2.18 | — |
| Calebin-A | | |
| 0.5 µg/ml | 41.24 ± 1.16* | 20.38%↓ |
| 1.0 µg/ml | 39.26 ± 2.52* | 24.20%↓ |
| 2.0 µg/ml | 37.16 ± 2.11** | 28.26%↓ |
| Rolipram (Standard) | | |
| 100 µg/ml | 22.52 ± 1.60** | 56.52%↓ |

Figure 6:
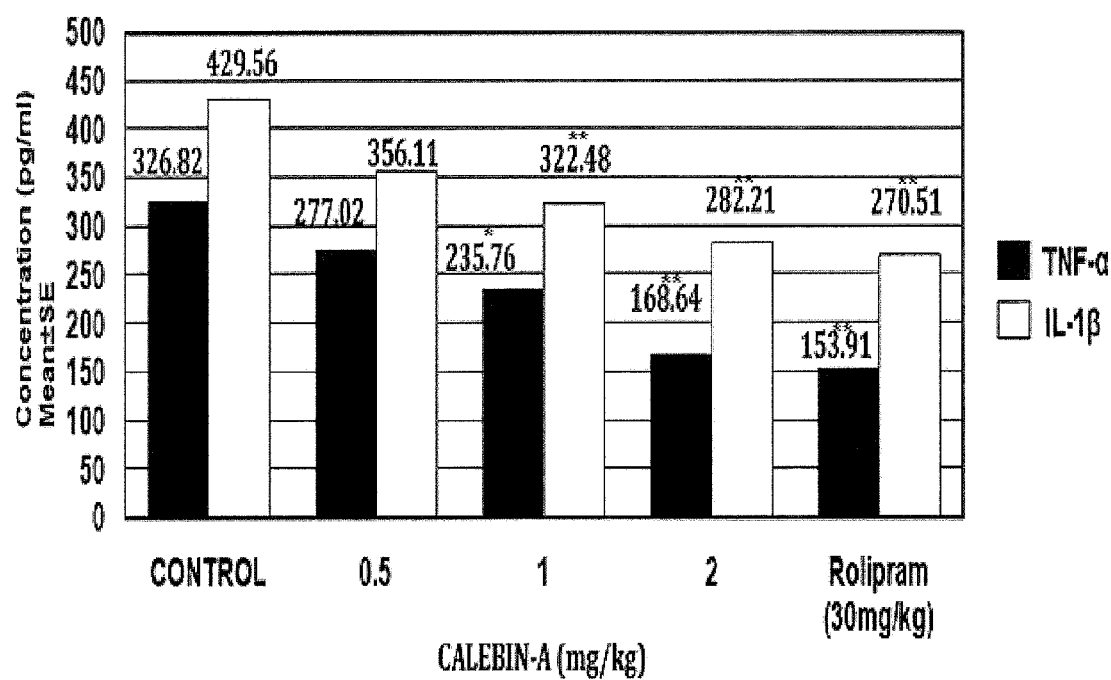
FIG. 6 shows the graphical representation of the effect of multiple dose of Calebin A on the expression of TNF-$\alpha$ and IL-1$\beta$ in the serum from treated Swiss Albino mice. No. of animals=6 per group, P-value: *<0.01; **<0.001 students 't' test.
Figure 7:
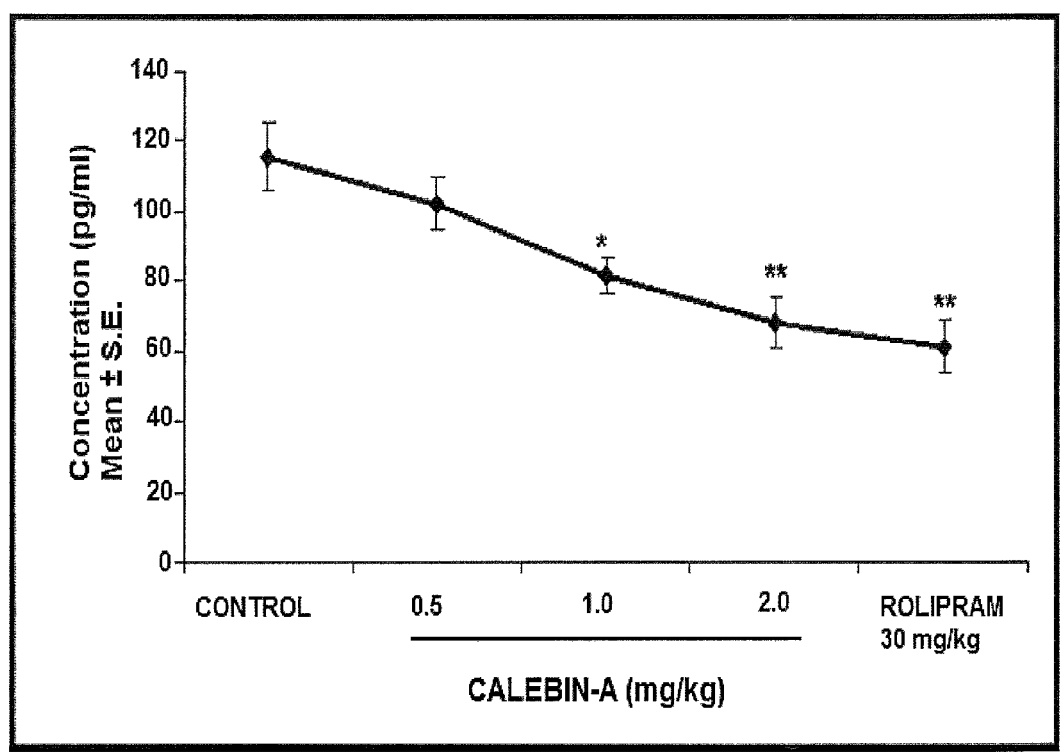
FIG. 7 shows the graphical representation of the effect of multiple dose of Calebin A on the expression of IL-6 in the serum from treated Swiss Albino mice. No. of animals=6 per group, P-value:*<0.01; **<0.001 students 't' test.

%↓: indicates suppression of IL-1 β expression
No. of observations = 3
P-value: *<0.01; **<0.001 students 't' test The present inventors also adduce study data on the ability of Calebin-A to reduce expression of Extracellular TNF-α, IL-1 beta [FIG. 6] and IL-6 [FIG. 7] in serum from treated mice (in-vivo models). Swiss albino male mice aged 6-8 weeks were maintained at 22±2° C. under 12/12 h light dark cycle. Mice received oral treatment of test drugs at graded doses (w/v) for 6 days, followed by intravenous injection of 1 mg/kg of LPS according to the method described by Brieva A, Guerrero A, Alonso-Lebrero J L and Pivel J P. 2001. Immunoferon, a glycoconjugate of natural origin, inhibits LPS-induced TNF-α production and inflammatory responses. International Immunopharmacology 1, 1979-1987. Six mice were employed in each group and experiments were performed in triplicates. TNF-α, IL-1 beta and IL-6 production was evaluated by a commercial ELISA kits (R&D Systems) in serum from treated mice, 90 min after LPS injection. Rolipram at 30 mg/kg was used as standard drug.

FIGS. 6 and 7 demonstrate that Calebin A is effective in reducing TNF-α, IL-1 beta and IL-6 thus indicating that the compound is a useful agent to modulate effects of local and systemic inflammation in obesity.

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method of inhibiting the terminal differentiation of mammalian adipocytes and associated adipogenesis (lipid accumulations) thereof with effective amounts of Calebin A, said method comprising the steps of
   a) Seeding mammalian adipocyte precursor cells (pre-adipocytes) in wells of microplates wherein approximately 60×104 cells are seeded for 48-72 hours to get 70-80% confluence;
   b) Adding 200 µl of freshly prepared Adipogenesis induction medium to the wells after 48 hours of incubation;
   c) Adding 200 µl of freshly prepared Adipogenesis progression medium with graded concentrations of Calebin A to the wells after 72 hours of incubation;
   d) Incubating the cells treated with graded concentrations of Calebin A for 48 hours in a humidified atmosphere (37 deg. C.) of 5% $CO_2$ and 95% air;
   e) Fixing the cells by adding 100 µl of 10% formalin and staining using the Oil Red O technique;
   f) Reading the optical density at 492 nm in a microplate reader and expressing the results as inhibitory concentration ($IC_{50}$) values using the graph pad prism software; and
   g) Calculating the percentage inhibition of adipogenesis in the cells using the formula,
   C-T/T×100, wherein C is the absorbance of Oil Red O in differentiating/undifferentiated cells and T is the absorbance of Oil Red O in sample treated differentiating/undifferentiated cells.

2. A method of inhibiting leptin expression in mammalian adipocytes with effective amounts of Calebin A, said method comprising the steps of
   a) Seeding mammalian adipocyte precursor cells (pre-adipocytes) in wells of microplates wherein approximately 60×104 cells are seeded for 48-72 hours to get 70-80% confluence;
   b) Adding 200 µl of freshly prepared Adipogenesis induction medium to the wells after 48 hours of incubation;
   c) Adding 200 µl of freshly prepared Adipogenesis progression medium with graded concentrations of Calebin A to the wells after 72 hours of incubation;
   d) Incubating the cells treated with graded concentrations of Calebin A for 48 hours in a humidified atmosphere (37 deg. C.) of 5% CO2 and 95% air; and
   e) Collecting cell supernatant and estimating leptin expression using Enzyme Linked Immunosorbent Assay (ELISA).

3. A method of increasing expression of adiponectin in mammalian adipocytes using effective amount of Calebin A, said method comprising the steps of
   a) Seeding mammalian adipocyte precursor cells (pre-adipocytes) in wells of microplates wherein approximately 60×104 cells are seeded for 48-72 hours to get 70-80% confluence;
   b) Adding 200 µl of freshly prepared Adipogenesis induction medium to the wells after 48 hours of incubation;
   c) Adding 200 µl of freshly prepared Adipogenesis progression medium with graded concentrations of Calebin A to the wells after 72 hours of incubation;
   d) Incubating the cells for 48 hours in a humidified atmosphere (37 deg. C.) of 5% CO2 and 95% air; and
   e) Collecting cell supernatant and estimation of adiponectin expression using ELISA.

4. A method of inhibiting obesity induced pro-inflammatory cytokines in mammalian adipocytes with effective amount of Calebin A, said method comprising the steps of
   a) Seeding mammalian adipocyte precursor cells (pre-adipocytes) in wells of microplates wherein approximately 60×104 cells are seeded for 48-72 hours to get 70-80% confluence;
   b) Adding 200 µl of freshly prepared Adipogenesis induction medium to the wells after 48 hours of incubation;
   c) Adding 200 µl of freshly prepared Adipogenesis progression medium with graded concentrations of Calebin A to the wells after 72 hours of incubation;

d) Incubating the cells treated for 48 hours in a humidified atmosphere (37 deg. C.) of 5% CO2 and 95% air; and e) Collecting cell supernatant and estimation of pro-inflammatory cytokine expression using Enzyme Linked Immunosorbent Assay (ELISA).

5. The method according to claim 4, wherein the pro-inflammatory cytokine is Tumor Necrosis Factor-α (TNF-α).

6. The method according to claim 4, wherein the pro-inflammatory cytokine is Interleukin-6 (IL-6).

7. The method according to claim 1 or 2, wherein the adipocytes are human adipocytes.

8. A method of reducing systemic expression of obesity related pro-inflammatory cytokines in mammals wherein said mammals are stimulated by obesity inducing lipopolysaccharides, said method comprising the steps of a) Maintaining appropriate mammals as for example, Swiss albino male mice aged 6-8 weeks at 22±2 deg.0 under 12/12 h light dark cycle;

b) Orally treating the mammals of step a. with graded doses (w/v) of test compound Calebin A for 6 days followed by intravenous injection of 1 mg/kg of lipopolysaccharides (LPS); and c) Estimation of pro-inflammatory cytokines in the serum of Calebin A treated mammals 90 minutes after LPS injection using Enzyme Linked Immunosorbent Assay (ELISA).

9. The method according to claim 8, wherein the pro-inflammatory cytokine is Tumor Necrosis Factor-α (TNF-α).

10. The method according to claim 8, wherein the pro-inflammatory cytokine is Interleukin-6 (IL-6).

11. The method according to claim 8, wherein the pro-inflammatory cytokine is Interleukin-1β (IL-1β).

12. The method according to claim 3 or 4, wherein the adipocytes are human adipocytes.

* * * * *